United States Patent
Barrus et al.

(10) Patent No.: US 8,945,189 B2
(45) Date of Patent: Feb. 3, 2015

(54) SPINAL FIXATION SYSTEM HAVING LOCKING AND UNLOCKING DEVICES FOR USE WITH A MULTI-PLANAR, TAPER LOCK SCREW

(71) Applicant: K2M, Inc., Leesburg, VA (US)

(72) Inventors: Michael Barrus, Ashburn, VA (US); Scott A. Jones, McMurray, PA (US); Kevin Strauss, Leesburg, VA (US)

(73) Assignee: K2M, Inc., Leesburg, VA (US)

( * ) Notice: Subject to any disclaimer, the term of this patent is extended or adjusted under 35 U.S.C. 154(b) by 0 days.

(21) Appl. No.: 13/711,727

(22) Filed: Dec. 12, 2012

(65) Prior Publication Data
US 2013/0110179 A1    May 2, 2013

Related U.S. Application Data

(63) Continuation of application No. 13/182,902, filed on Jul. 14, 2011, now Pat. No. 8,361,122, which is a continuation of application No. 11/493,624, filed on Jul. 27, 2006, now Pat. No. 7,988,694.

(60) Provisional application No. 60/721,482, filed on Sep. 29, 2005.

(51) Int. Cl.
*A61B 17/70* (2006.01)
*A61B 17/86* (2006.01)

(52) U.S. Cl.
CPC ............ *A61B 17/861* (2013.01); *A61B 17/7032* (2013.01); *A61B 17/7035* (2013.01); *A61B 17/7037* (2013.01); *A61B 17/7086* (2013.01); *A61B 17/7011* (2013.01)
USPC ......................................................... 606/266

(58) Field of Classification Search
USPC ....... 606/246, 264–279, 300–306, 320, 86 A, 606/99
See application file for complete search history.

(56) References Cited

U.S. PATENT DOCUMENTS

| | | | |
|---|---|---|---|
| 4,950,269 A | | 8/1990 | Gaines, Jr. |
| 5,683,392 A | * | 11/1997 | Richelsoph et al. .......... 606/272 |
| 6,010,503 A | | 1/2000 | Richelsoph et al. |
| 6,413,258 B1 | | 7/2002 | Bernhardt, Jr. |
| 6,648,888 B1 | | 11/2003 | Shluzas |
| 7,090,674 B2 | | 8/2006 | Doubler et al. |
| 7,105,029 B2 | | 9/2006 | Doubler et al. |
| 7,118,303 B2 | | 10/2006 | Doubler et al. |
| 7,334,961 B2 | | 2/2008 | Doubler et al. |
| 7,335,201 B2 | | 2/2008 | Doubler et al. |
| 7,445,627 B2 | | 11/2008 | Hawkes et al. |
| 7,658,582 B2 | | 2/2010 | Doubler et al. |
| 7,678,136 B2 | | 3/2010 | Doubler et al. |
| 2004/0147937 A1 | | 7/2004 | Dunbar et al. |
| 2004/0158247 A1 | | 8/2004 | Sitiso et al. |
| 2005/0049589 A1 | | 3/2005 | Jackson |

(Continued)

*Primary Examiner* — Eduardo C Robert
*Assistant Examiner* — Steven Cotroneo
(74) *Attorney, Agent, or Firm* — Carter DeLuca Farrell & Schmidt, LLP

(57) ABSTRACT

Provided is a spinal fixation system including a taper lock screw including an inner housing and an outer housing that are translatable relative to one another to transition the taper lock screw between a locked position and an unlocked position. A locking device releasably connects to and operationally interacts with a flange of the taper lock screw. An unlocking device releasably connects to and operationally interacts with inner housing unlocking tool receptors of the taper lock screw to unlock the taper lock screw.

20 Claims, 12 Drawing Sheets

(56) References Cited

U.S. PATENT DOCUMENTS

| | | |
|---|---|---|
| 2005/0053423 A1 | 3/2005 | Doubler et al. |
| 2005/0149048 A1 | 7/2005 | Leport et al. |
| 2006/0200132 A1 | 9/2006 | Chao et al. |
| 2006/0276792 A1* | 12/2006 | Ensign et al. .................. 606/61 |
| 2007/0286703 A1 | 12/2007 | Doubler et al. |
| 2008/0137933 A1 | 6/2008 | Kim |
| 2008/0243193 A1* | 10/2008 | Ensign et al. ................ 606/305 |

* cited by examiner

SPINAL FIXATION SYSTEM HAVING LOCKING AND UNLOCKING DEVICES FOR USE WITH A MULTI-PLANAR, TAPER LOCK SCREW

CROSS REFERENCE TO RELATED APPLICATIONS

This application is a continuation of U.S. patent application Ser. No. 13/182,902, filed on Jul. 14, 2011, now U.S. Pat. No. 8,361,122, which is a continuation of U.S. patent application Ser. No 11/493,624, filed on Jul. 27, 2006, now U.S. Pat. No. 7,988,694, which claims the benefit of U.S. Provisional Patent Application Ser. No. 60/721,482 filed on Sep. 29, 2005, the entire contents of each of which are incorporated herein by reference.

BACKGROUND

1. Technical Field

The present invention relates to orthopedic surgery, and in particular to devices for stabilizing and fixing the bones and joints of the body. Particularly, the present invention relates to a spinal fixation system that includes surgical instruments that can be used for locking or unlocking a taper lock screw, the screw preferably being multi-planar and useful for securing a spinal rod or plate to a vertebra.

2. Background of Related Art

The spinal column is a complex system of bones and connective tissues that provides support for the human body and protection for the spinal cord and nerves. The adult spine is comprised of 24 vertebral bodies, which are subdivided into three areas including seven cervical vertebrae, 12 thoracic vertebrae and five lumbar vertebrae. Between each vertebral body is an intervertebral disc that cushions and dampens the various translational and rotational forces exerted on the spinal column.

There are various disorders, diseases and types of injury which the spinal column may experience in a lifetime. The problems may include but are not limited to scoliosis, kyphosis, excessive lordosis, spondylolisthesis, slipped or ruptured discs, degenerative disc disease, vertebral body fracture, and tumors. Persons suffering from any of the above conditions typically experience extreme or debilitating pain and often times diminished nerve function.

One of the more common solutions to any of the above mentioned conditions involves a surgical procedure known as spinal fusion. A spinal fusion procedure involves fusing two or more vertebral bodies in order to eliminate motion at the intervertebral disc or joint. To achieve this, natural or artificial bone, along with a spacing device, replaces part or all of the intervertebral disc to form a rigid column of bone and mechanical hardware. In this way damaged or diseased vertebrae are connected to healthy adjacent vertebrae to stabilize the spine while the bone grows and fusion takes place.

The mechanical hardware used to immobilize the spinal column typically involves a series of bone screws and metal rods or plates. When the spine surgery is posteriorly performed, it is common practice to place bone screws into the vertebral bodies and then connect a metal rod between the bone screws thus creating a rigid structure between adjacent vertebral bodies. When the spine surgery is performed anteriorly, it is common practice to attach a thin metal plate directly to the vertebral bodies and secure it to each vertebral level using one or more bone screws.

Many conventional devices for locking a spinal rod to a fixation hook or screw do not offer the needed variability to allow the spinal rod to be easily connected to adjacent vertebrae, which are not aligned on the same plane. In some cases the use of these devices may be permanently implanted in the subject. In other cases, the devices may be implanted only as a temporary means of stabilizing or fixing the bones or bone fragments, with subsequent removal when no longer needed. It is also common that device implants that were intended to be permanent may require subsequent procedures or revisions as the dynamics of the subject's condition warrant. For these reasons, it is desirable that an implanted device be provided, which can be easily locked and unlocked as desired by the surgeon.

In recent years some effort has been made to provide taper lock bone screws and further to provide taper lock bone screws that are multi-planar; however, even when multi-planar type bone screws have been developed, the use of those screws has proven difficult because the locking and unlocking instruments that are used by the surgeon during the surgical procedure are of a generic design and inadequate to quickly lock or unlock the bone screws. In addition, with prior conventional screws the mode of locking the screw and rod typically involves set screws or nuts, the application and tightening of which generates twisting or torsional forces, i.e., torque, which are transmitted through the screw to the bone to which the screw has been inserted. Such torsional forces can alter the disposition of the screw in the bone or can damage the bone, which may be of poor strength or quality in patients undergoing surgery. As such, the torsional forces can adversely affect the outcome of the procedure.

To meet the problem of securely connecting adjacent vertebrae, not on a common plane, a requirement exists to provide a multi-planar, taper lock screw that can be easily inserted and easily removed from the vertebral bone as desired and to provide the specialized instrumentation that can facilitate quick locking and unlocking of such a screw. It is also desirable that such a screw and the instrumentation for locking and unlocking the screw be configured so that the screw can be locked into position in relation to the bone and the spinal rod without the need to exert any additional torque to the screw. Additionally, the development of such a multi-planar screw and the locking and unlocking instrumentation can be designed so as to eliminate the need for an additional locking piece, such as the conventional, often difficult to manipulate set screw or nut that is a small separate element from the bone screw and normally requires threading with the application of torque onto the screw.

Conventional efforts to meet this need have fallen short in that no systematic approach has been provided that adapts the spinal rod to the multi-planar environment of the spine by using a multi-planar locking bone screw with specifically designed locking and unlocking instruments that present a quick, torqueless method of locking and unlocking the rod to the screw. Thus, while much attention is generally given to developing improved implants, the benefits of the innovations are often not fully realized because the appropriate instrumentation is not developed in a parallel systemic fashion.

For this reason, a major challenge of spine surgery is in the development of surgical instruments or instrumentation, for the surgeon to use during the implantation of the mechanical fixating structure. The instrumentation must be easy to use, effective, durable and most importantly, must not interfere with or cause further damage to the patient's anatomy.

While surgical instrumentation can sometimes be generic and effectively used in a variety of procedures, it is becoming more prevalent that the instrumentation is designed to be part of a specific system or procedure; that is, the instrumentation is designed to work best with certain implants.

Often implants are difficult to access and grasp with instruments thus increasing the surgeon's workload and prolonging the amount of time that the patient is in surgery. As improvements are made in the spinal implants themselves, it is often found that existing or generic instruments are inadequate to the task of effectively and efficiently manipulating the spinal implant. This is particularly troublesome when attempting to reduce a spinal rod into a receiving portion of an implant such as a pedicle screw or attempting to later release the spinal rod from that screw.

For these reasons there remains a need for a device which, in one simple action such as squeezing a lever, can reduce a posteriorly introduced rod into a pedicle screw and securely lock the rod into the pedicle screw. Conversely, there remains a need for a similar device which, through an equally simple action, can unlock a pedicle screw thereby releasing the posteriorly introduced rod.

SUMMARY

The present system provides novel component devices and a method for selectively locking and unlocking a spinal rod to a bone screw using easily operated, torqueless locking and unlocking devices or instruments that are specifically designed for use with a novel taper lock screw.

Also provided is a system that includes several devices including a novel taper lock screw, which is preferably a multi-planar taper lock screw, a torqueless, easily operated locking instrument, and a torqueless, easily operated unlocking instrument.

Also provided is a multi-planar taper lock screw that is configured to be releasably connected to a spinal rod at the uppermost portion of the screw and physically connected to a first vertebra using the lower threaded portion of the screw. The multi-planar aspect of the screw enables it to be used to make such a connection to a rod that can also be connected to an adjacent vertebra not in the same plane as the first vertebra. The multi-planar taper lock screw has a novel configuration that includes a proximally located easily accessed flange. That proximal flange with other specifically designed structural elements of the screw is configured to facilitate grasping of the screw by a locking and/or unlocking instrument that can insert and lock a spinal rod securely into place in the screw or selectively unlock the rod from the screw using complementary designed unlocking instruments.

Also provided is a locking instrument that includes complementary configured operational features to that of the multi-planar taper lock screw. The locking instrument is designed to facilitate the inserting and torqueless locking of a rod, such as a spinal rod, into a selectively locked/unlocked connecting rod slot on the uppermost portion of the multi-planar taper lock screw.

Also provided is an unlocking instrument that is configured with complementary features to that of the multi-planar taper lock screw. The unlocking instrument is designed to facilitate the torqueless unlocking and release of a rod, such as a spinal rod, from a selectively locked/unlocked connecting rod slot on the upper most portion of the multi-planar taper lock screw.

Also provided is a system that includes a novel multi-planar taper lock screw configured to have a slidable outer housing over an inner housing containing a spherically configured screw head around which an articulating recess of the inner housing articulates and a connecting rod slot of the inner housing within which a removable spinal rod can be manipulated; the outer housing being capable of being selectively positioned relative to the inner housing so as to fully lock the screw head and the spinal rod in position within the inner housing. The system also includes specifically designed locking and unlocking devices or instruments.

Also provided is a system that includes a novel multi-planar taper lock screw configured to have a slidable outer housing over an inner housing containing a spherically configured screw head around which the inner housing can pivot and a removable spinal rod wherein the outer housing can be selectively positioned to fully lock the screw head and the spinal rod in position within the inner housing or can be selectively positioned to lock only the screw head in position while permitting a sliding and rotating motion of the spinal rod about its long axis within the inner housing.

Also provided is a kit that can include at least two of the novel multi-planar taper lock screws, at least one rod device, and the novel, complementary configured locking and unlocking instruments.

Also provided is a method of using the novel system to fixate a portion of a spinal column using one or more multi-planar taper lock screws and selectively using the complimentarily configured locking or unlocking devices, wherein the surgical procedure employed, in comparison to conventional methods, is quickly accomplished for locking or unlocking of the rod from the screw without applying additional torque to the screw.

These and other embodiments of the present disclosure will be described in detail below with reference to the accompanying figures.

BRIEF DESCRIPTION OF THE DRAWINGS

Embodiments of the present disclosure are described herein with reference to the accompanying drawings, wherein.

DETAILED DESCRIPTION

Detailed embodiments are disclosed herein; however, it is understood that the following description is provided as being exemplary of the invention, which may be embodied in various forms without departing from the scope of the claimed invention. Thus, the specific structural and functional details provided in the description are non-limiting, but serve merely as a basis for the invention defined by the claims provided herewith.

Figure 1:
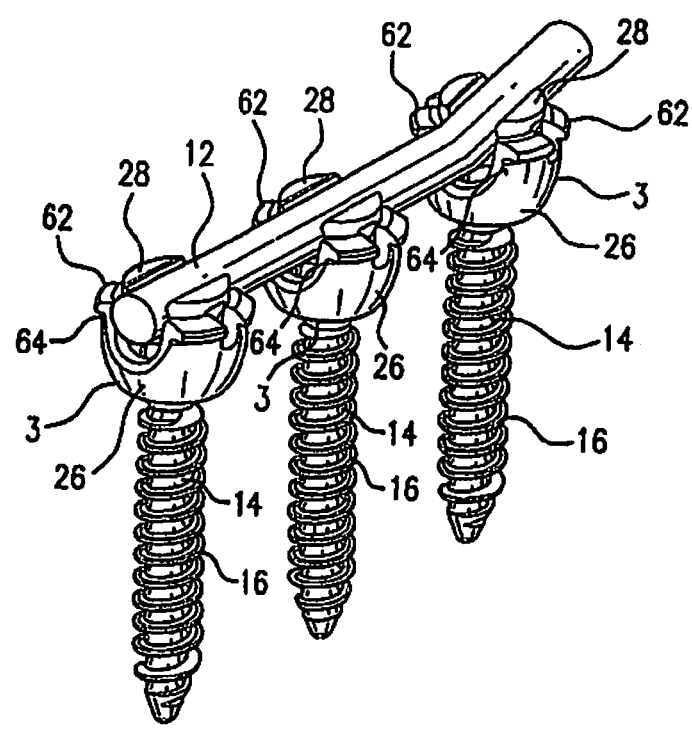
FIG. 1 shows a perspective view of a surgical rod positioned within the connecting rod slot of each of three multi-planar taper lock screws, the screws being in an unlocked mode.

FIG. 1 illustrates an example of a unilateral orthopedic fixation assembly that includes a connecting rod 12 and three separate screw components 3. In the example shown, the connecting rod 12 is a spinal rod having a generally circular cross section; however, it is within the concept of the invention to secure connecting rods of any suitable cross-sectional configuration required for the need at hand.

The System

Figure 2A:
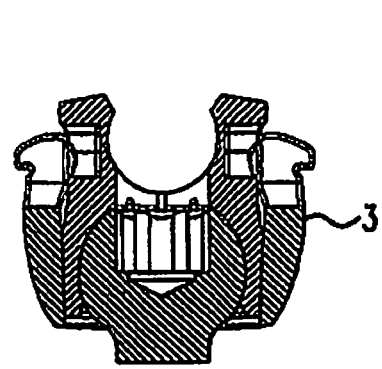
FIGS. 2A, 2B, 2C, and 2D show components of the system including a cross-sectional view of the multi-planar taper lock screw (FIG. 2A unlocked and FIG. 2B locked with a spinal rod in place), a locking device (FIG. 2C) and an unlocking device (FIG. 2D), each of the locking and unlocking devices being specifically and distinctly configured for use with the multi-planar taper lock screw so as to selectively lock or unlock a spinal rod therefrom.
Figure 2B:
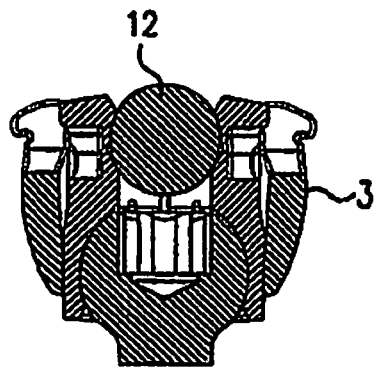
Figure 2C:
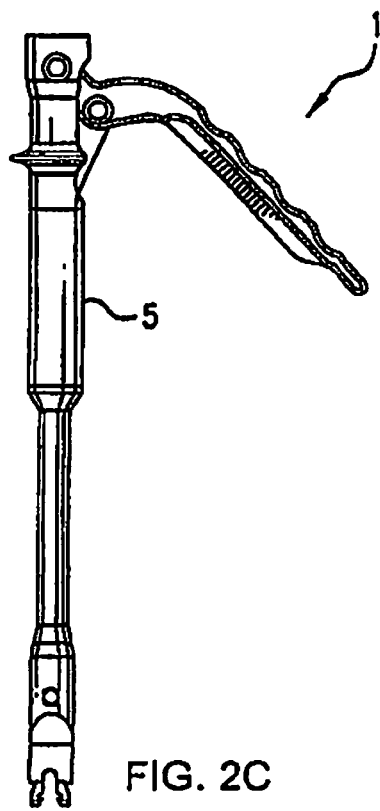
Figure 2D:
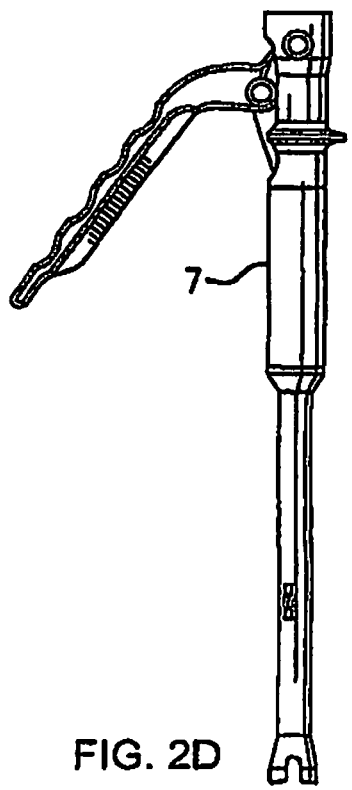

The novel spinal fixation system is generally shown at 1 in FIGS. 2A-D. FIG. 2A shows the screw component of the system 1 in an unlocked configuration and FIG. 2B shows the same component in a locked configuration. FIG. 2C and FIG. 2D respectively show the unlocking component and the locking component of the novel spinal fixation system 1. The system 1 can be used to implant and lock in place a fixation assembly, such as that represented by the non-limiting example shown in FIG. 1. The system 1 includes a novel bone screw 3, which is best shown in FIGS. 1, 2A-2B, 3A-3B, 4A-4B, 8 and 12. The bone screw is a taper lock screw that can be mono-axial or multiplanar. If the screw is a mono-axial taper lock screw, the longitudinal axis of the screw shaft 14 coincides with the longitudinal axis of the screw 3. Preferably the screw 3 of the system 1 is a multi-planar taper lock screw, which allows manipulation of the screw shaft about all three axes. The system also includes a novel unlocking device or instrument component 5 and a novel locking device or instrument component 7, each of which is specifically designed to respectively conform to the configuration of the unlocking and locking elements of the screw 3 and to operationally interact therewith. The screw 3 is configured and dimensioned so as to facilitate ease of insertion of the screw 3 into bone and connection to surgical devices such as spinal rods 12 as well as facilitating easy locking and unlocking by selectively engaging the screw 3 with the other system components, the unlocking device 5 and the locking device 7, respectively. The components of the system 1 are capable of selectively providing a partial lock or a full lock of the screw component 3.

The Screw Component

The screw component of the system 1 can be a mono-axial taper lock screw or a multiplanar taper lock screw. As best shown in FIGS. 1-4A-B, 8, and 12, the preferred multi-planar tapered locking screw 3 includes a screw shaft 14, which defines an external helical thread 16 for penetrating bone through the application of torque. The upper portion of the screw shaft 14 terminates in a screw head 18, which is generally spherical in part and at its uppermost surface 20 defines a screw head recess 22, which has a recess surface configuration that is complementary to the shape of a tightening and/or loosening tool. By way of example only, the screw head recess may engage a screw driver or more specifically a hex screw driver (not illustrated). Without departing from the concept of the present invention, the screw head recess 22 can also be configured as a protrusion rather than a recess provided that the protrusion has a surface that is complementary for gripping attachment to a tool for tightening and/or loosening and provided that the height of the protrusion above the uppermost surface 20 of the screw head 18 is not such that it obstructs or interferes with any of the functions of the screw 3. In this regard, it is contemplated that a screw driving protrusion attached to and extending upward from the screw head may be gripped by a wrench or socket driver to apply torque to drive the screw into bone. Of course, the bone into which the screw is driven may be prepared in advance of inserting the screw in any suitable manner within the discretion of the surgeon such as by drilling and optionally tapping a hole to receive the screw.

Figure 3A:
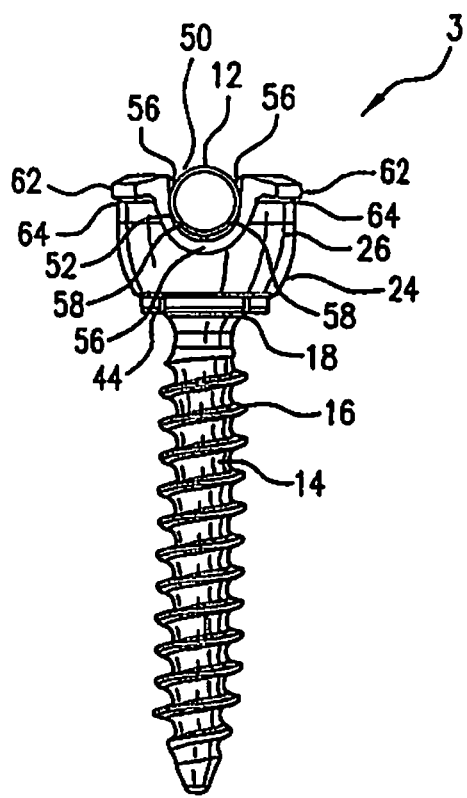
FIG. 3A shows a side view of the screw component of the system, the screw being configured in a locked or closed position, that is with the surgical rod locked in place within the inner housing of the screw.
Figure 3B:
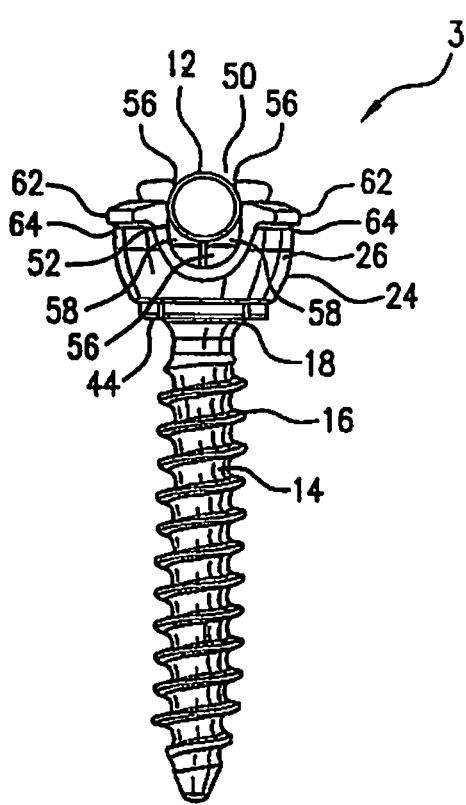
FIG. 3B shows a side view of the screw component of the system, the screw being configured in an unlocked or open position, that is with a surgical rod in place within the screw but not locked and secured therein.
Figure 4A:
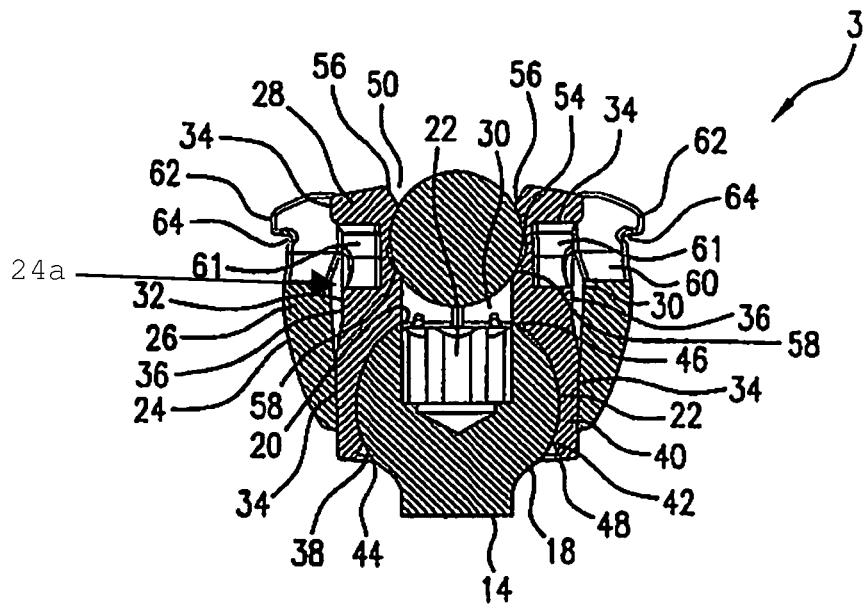
FIG. 4A shows a cross-sectional view of the body portion of the screw component of the system in a closed position, that is with a surgical rod secured and locked in the screw body.
Figure 4B:
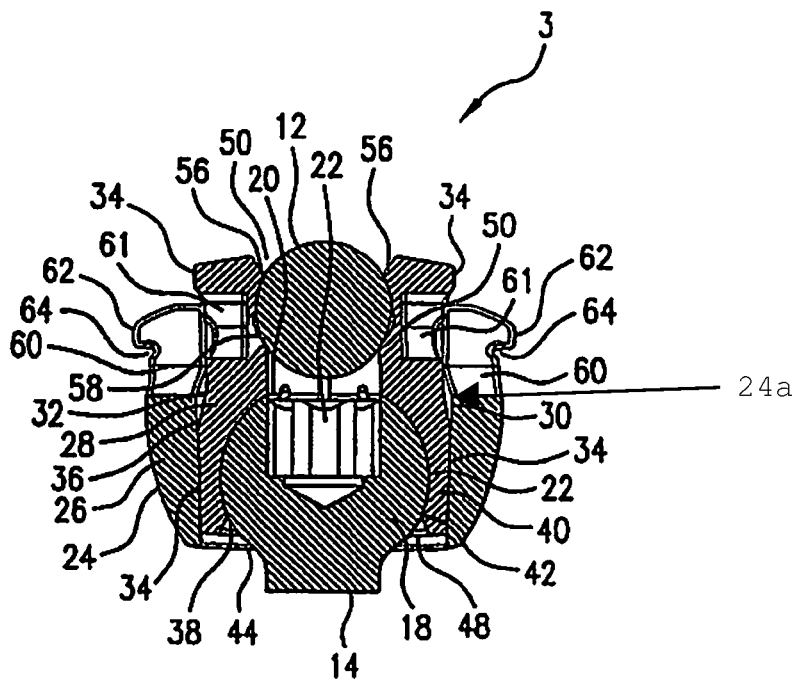
FIG. 4B shows a cross-sectional view of the body portion of the screw component of the system in an open position, that is with a surgical rod in place within the screw body but not locked and secured thereto.
Figure 5:
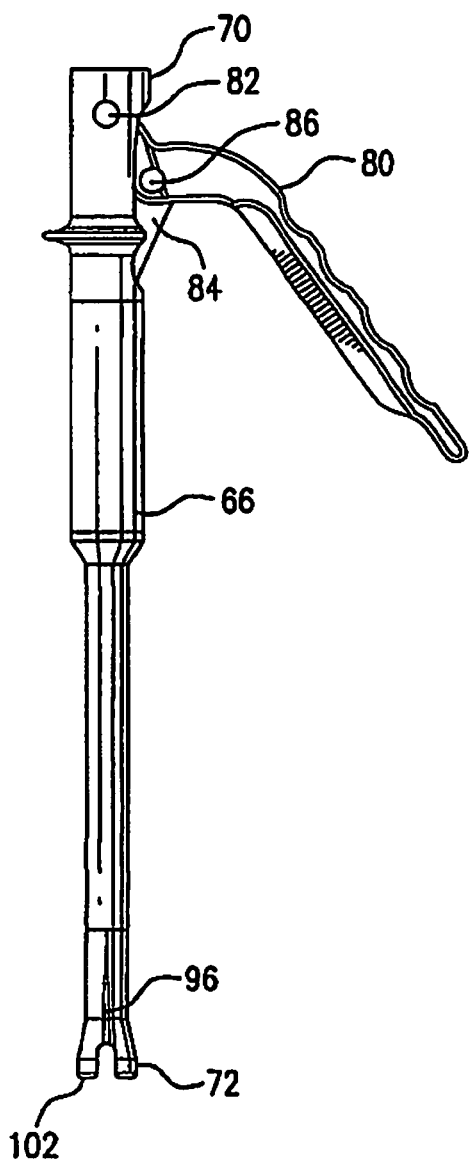
FIG. 5 shows a side view of a bone screw locking device component of the system.
Figure 6:
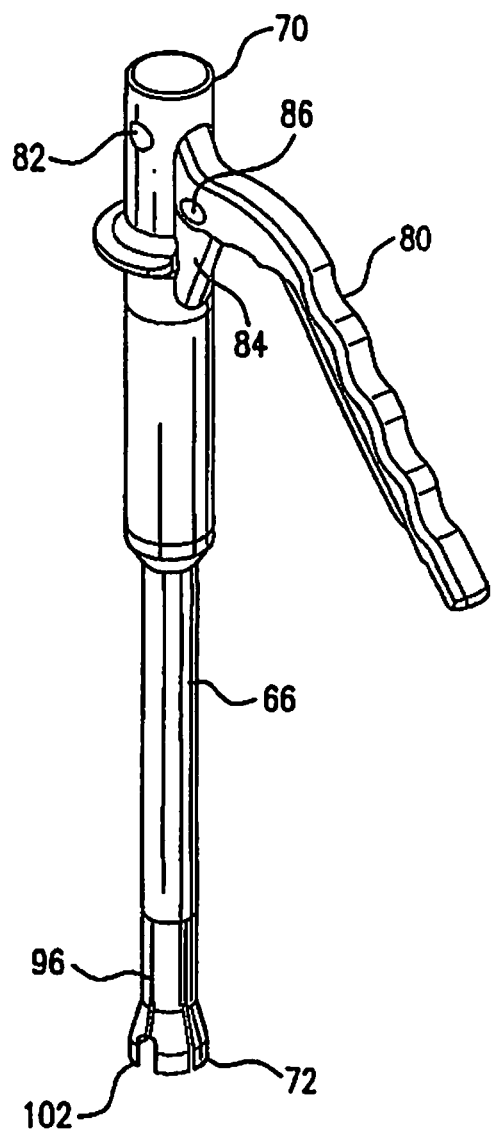
FIG. 6 shows an isometric view of a bone screw locking device component of the system.
Figure 8:
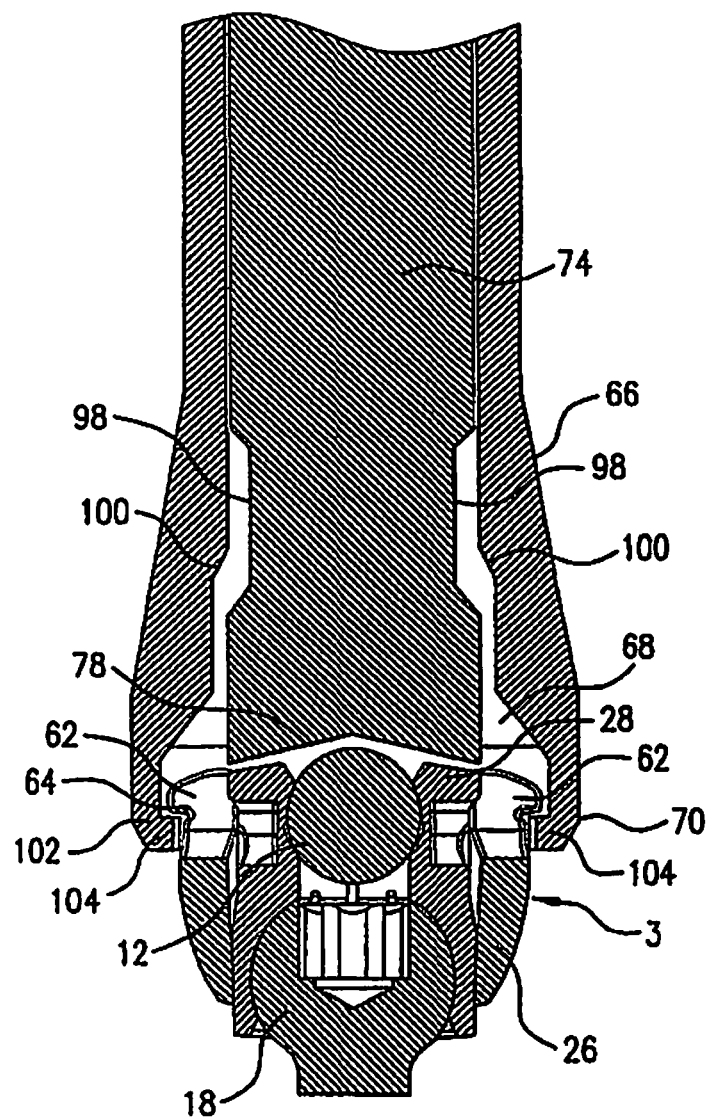
FIG. 8 shows a cross-sectional view of the lower portion of the bone screw locking device component operationally engaged with the screw component in a locked configuration.
Figure 12:
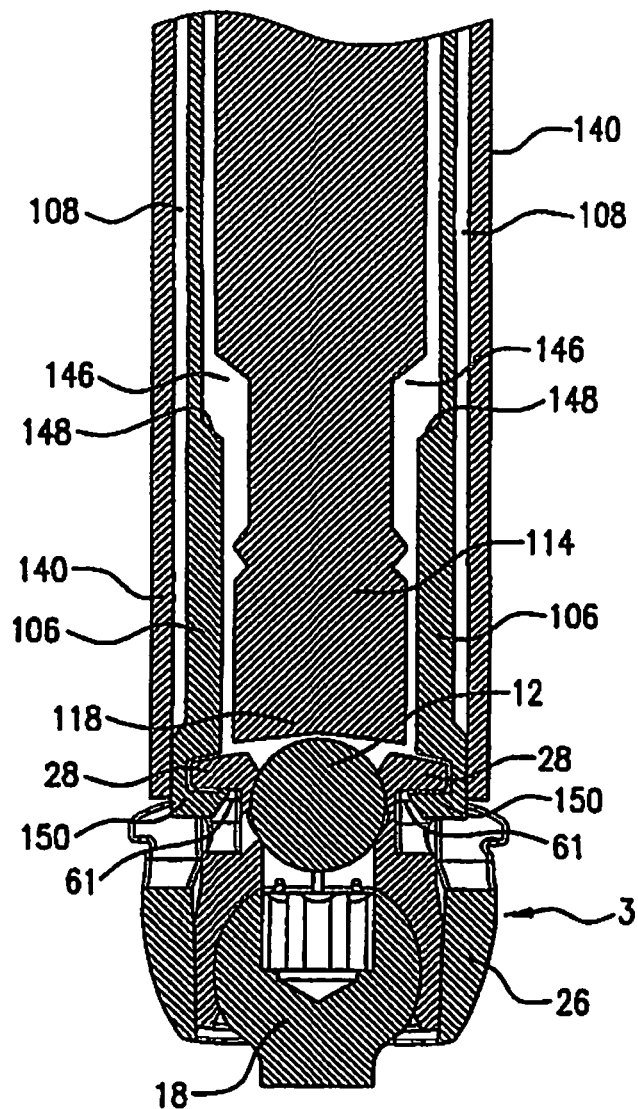
FIG. 12 shows a cross-sectional view of the lower portion of the bone screw unlocking device component operationally engaged with the screw component in an unlocked configuration.

As best shown in FIG. 1, the screw 3 is capable of connecting a connecting rod 12 to multiple vertebrae, which are aligned in the spinal column on different planes due to the natural curvature of the spine. As best shown in FIGS. 3A-3B and 4A-4B, the screw 3 component of the system 1 includes a dual layered screw housing 24 that includes an outer housing 26 and an inner housing 28. With reference to FIGS. 4A and 4B, the outer housing 26 and the inner housing 28 define the gap 24a therebetween. The outer housing 26 is configured such that at least a portion of the inner surface 30 of the outer housing 26 is capable of selectively sliding over a portion of the outer surface 32 of the inner housing 28 in an upward and downward direction along the longitudinal axis of the screw 3. As the outer housing 26 slides in the upward direction relative to the inner housing 28, the screw 3 moves from an unlocked position (FIG. 4B) to a locked position (FIG. 4A) such that dimensions of the gap 24a increase. By comparison, as the outer housing 26 slides in the downward direction relative to the inner housing 28, the dimensions of the gap 24a decrease. Accordingly, the dimensions of the gap 24a are largest in the locked position (FIG. 4A) of the screw 3 and the smallest in the unlocked position (FIG. 4B) of the screw 3, As best shown in FIGS. 8 and 12, the locking device 7 component and the unlocking device 5 component of the system 1 are specifically configured to quickly engage with the screw 3 component and thus facilitate this upward locking or downward unlocking sliding motion of the outer housing 26 relative to the inner housing 28. The configuration of both the outer housing 26 and the inner housing 28 are complementary, one to the other, in that when the outer housing is slid upward in relation to the inner housing at least one outer housing internal compression contact surface 34 is brought to bear against at least a portion of the outer wall 36 of the inner housing 28 and by that compressive force causes the inner housing 28 in turn to mechanically transmit that compressive force inward toward the central longitudinal axis of the screw 3.

A screw head articulation recess 38 is defined in the interior of the lower portion 40 of the inner housing 28. The interior surface 42 of the articulation recess 38 has a complementary surface configuration to the generally spherical shape of the screw head 18 so as to facilitate multi-planar rotational articulation of the screw head 18 within the recess 38. The lower most portion of the inner housing 28 defines a screw shaft exit portal 44, that is sized small enough to retain the spherical screw head 18 within the recess 38 but that is large enough to allow multi-directional movement of the screw shaft that extends exterior to the inner housing 28. The recess 38 can include a recess upper edge 46 that is configured to selectively exert a locking compressive force against the screw head 18 when the locking device 7 is operationally employed with the screw 3. A recess lower edge 48 can also be provided for the same purpose. It is also contemplated that all or portions of the interior wall of the recess 38 can selectively provide the compressive force against the screw head 18 that is sufficient to hold the screw head in a locked position.

The upper portion of the inner housing 28 defines an inner housing connecting rod slot 50 that is sized and configured to permit a connecting rod 12 to be placed transversely within the upper portion of the inner housing 28. An outer housing connecting rod slot 52 can be provided that is in common alignment with the inner housing connecting rod slot but is not necessarily of exactly the same dimension as the inner housing slot 50. The inner housing connecting rod slot 50 can define at least one compression contact surface 54 that when forced into compressive contact with a connecting rod 12 present in the slot 50, serves to securely lock and hold the rod 12 in its relative position to the inner housing 28. As discussed in greater detail below, this required force is provided by the operational engagement of the locking device 7 with the screw 3 that results in an upward sliding motion of the outer housing 26 relative to the inner housing 28. Preferably the inner housing connecting rod slot 50 is provided with an opposing upper compression contact surface 56 and an opposing lower compression contact surface 58, which together can selectively be forced against the connecting rod 12 so as to secure and lock it in place within the inner housing 28.

Preliminary to operation of the screw 3, the outer housing 26 should be positioned in the open position; that is it should be slid downward relative to the inner housing 28 (see FIG. 2A). The screw shaft 14 can then be driven into the cancellous bone by providing torsional force via a tool configured to mate with and grip the screw head recess 22. After the screw shaft 14 is positioned within the bone and the driving tool removed from the screw 3, a connecting rod 12 can be positioned transversely along the common course of and within the inner housing connecting rod slot 50 and the outer housing connecting rod slot 52 (see FIGS. 1, 3B and 4B). With the screw shaft 14 and screw head 18 being fixed in position relative to the bone, the inner housing 28 and the circumferentially disposed outer housing 26 can be articulated relative to the screw head 18 as necessary to manipulate the disposition of the connecting rod 12 within the screw 3. Upon completion of the necessary positional adjustments of the inner housing recess 38 relative to the screw head 18 and the adjustments of the connecting rod 12 relative to the inner housing connecting rod slot 50, the outer housing 26 can be grasped by the operator using the complementary configured locking device 7. Activation of the locking device 7 slides the outer housing 26 upward circumferentially over the outer surface of the inner housing 28 while the push rod 74 holds down the connecting rod 12 and the inner housing 28 so that the screw is reconfigured from the open or unlocked position, as shown in FIGS. 3B and 4B, to the closed or locked position, as shown in FIGS. 3A and 4A. Similarly, the operator can use the complementary configured unlocking device 5 to grasp the inner housing 28 and slidably move the outer housing downward along the outer surface of the inner housing 28 from a closed or locked position, as shown in FIGS. 3A and 4A, to an open or unlocked position, as shown in FIGS. 3B and 4B. The screw 3 can be provided with an inner housing access slot 60 defined through the wall of the outer housing 26, which provides access for the unlocking device 5 that is designed to make grasping contact with an inner housing tool receptor 61 to facilitate quickly unlocking the screw 3 to a mode permitting movement of the screw head 18 within the articulation recess 38 and removal of the connecting rod 12 from the inner housing connecting rod slot 50.

The outer housing 26 is provided with a receiving element 62 for the locking device 7, the receiving element 62 being formed by an outward extension of the upper portion of the outer surface of the outer housing 26. Preferably, the receiving element is a proximally located annular flange 62, which is formed as a generally radial extension from the upper third portion of the outside surface of the outer housing 26. More preferably, the annular flange 62 radially extends from a more elevated and therefore more operator accessible position from the upper quarter of the outer housing 26. Even more preferably, the annular flange 62 can extend from the upper fifth or less of the outer housing so long as the structural integrity of the flange connection to the outer housing during use is maintained. By way of example, if the outer housing has a height of approximately 0.76 inches, the lower lip of the flange would be approximately 0.40 inches from the top surface of the outer housing. This elevated position of the annular flange 62 provides a distinct advantage to the operator by positioning the annular flange 62 above any possible interference of anatomy contact or view obstruction when the surgeon is attempting to access the screw and connect it to the locking device 7 during the insertion and locking of the screw 3. As best shown in FIGS. 2A-2B, 3A-B, and 4A-B, the annular flange can be configured as a descending tapered lip around at least a part of the circumference of the upper portion of the outer housing. While the preferred annular flange 62 is proximally connected or integrally formed at the upper portion of the outer housing 26 and preferably formed within the upper third of the vertical length of the outer housing, it is contemplated that the locking device and unlocking device disclosed herein may be used with a taper lock screw in which the annular flange 62 or other gripping features (such as slots or holes) on the outer housing are more distally disposed. The receiving element 62 can include an annular gripping groove 64, which is preferably located directly beneath the annular flange 62, which is best shown in FIGS. F1, 2A-2B, 3A-B, and 4A-B. The annular gripping groove 64 can serve to strengthen the operational connection of the locking device 7 to the screw 3. Similar to the annular flange 62, the annular gripping groove 64 preferably is present along at least a portion of the outer surface of the outer housing 26.

The locking device 7 and unlocking device 5 may be used to selectively connect to the screw 3 and to then position the outer housing 26 along the surface of the inner housing 28 such that the compressive force exerted by the outer housing 26 on the inner housing 28 is such that a partial lock position can be attained; that is, by a limited sliding movement of the outer housing 26 relative to the inner housing 28, partial compressive pressure will be exerted on the articulation recess 38 and the screw head 18 positioned therein as well on the inner housing connecting rod slot 50 and the connecting rod 12 positioned therein. The partial compressive pressure of the partial lock mode allows repositioning of the articulating recess 38 around the screw head 18 as well as position adjustment of the rod 12 within the inner housing connecting rod slot 50. Using this partial lock of the screw 3, the operator can first position the screw 3 relative to the bone into which the screw shaft 14 has been attached and then manipulate the inner housing 28 relative to the screw head 18 and relative to the connecting rod 12 to optimize screw and rod position before sliding the outer housing 26 into a fully locked position on the inner housing 28. In an exemplary embodiment, this partial locking of the screw head 18 and the connecting rod 12 can be achieved when the outer housing 26 has been moved upward about 25 percent of its total possible sliding distance along the outer surface of the inner housing 28, that is, 25 percent of the sliding distance from the fully unlocked to the fully locked position. In such an exemplary embodiment, when the outer housing 26 is slid further up along the outer surface of the inner housing 28 to a position approximately 45 percent of the total possible sliding distance, the screw head articulating recess 38 will be more tightly compressed against and fully locking in relation to the screw head 18 while the compression forces against the more superiorly disposed connecting rod 12 will be such as to contain the connecting rod in the screw 3 but still permit adjusting manipulation of the connecting rod 12 within the inner housing connecting rod slot 50. In the exemplary embodiment, further upward sliding movement of the outer housing 26 over the surface of the inner housing 28 to a position approximately 100 percent of the total possible sliding distance will apply stronger compressive forces on both the screw head 18 and the connecting rod 12 so that the screw 3 will be in a fully locked position. As best shown in FIGS. 3A and 4A, when the outer housing 26 is slid upward along the outer surface 32 of the inner housing 28 such that the screw 3 is in a fully locked or closed position, the uppermost extent of the outer housing 26 and the annular flange 62 are in a general alignment with the uppermost extent of the inner housing 28. In addition, with screw 3 in the fully locked position the top of connecting rod 12 also is generally aligned with the uppermost extent of outer housing 26, the uppermost extent of inner housing 28 and the upper most extent of the proximal flange. As can be seen in FIGS. 3A and 4A, this provides a screw in a locked position in which there is substantially no profile above the connecting rod. This feature advantageously reduces the structure of the screw above the rod which might otherwise contact adjacent anatomical structures and cause pain or discomfort. The degree of this general alignment of the uppermost pails of the outer housing 26 and the inner housing 28 when the screw 3 is fully locked is demonstrated by comparison to the position of the uppermost parts of the outer housing 26 and inner housing 28 in the unlocked position, as shown in FIGS. 3B and 4B. Unlike conventional screws, the upper most part of the present screw 3 does not substantially extend beyond the upper level of the connecting rod held therein and further, does not require the additional attachment of locking set screws or nuts that in conventional systems are attached above the level of the connecting rod.

The Locking Device Component.

Figure 7A:
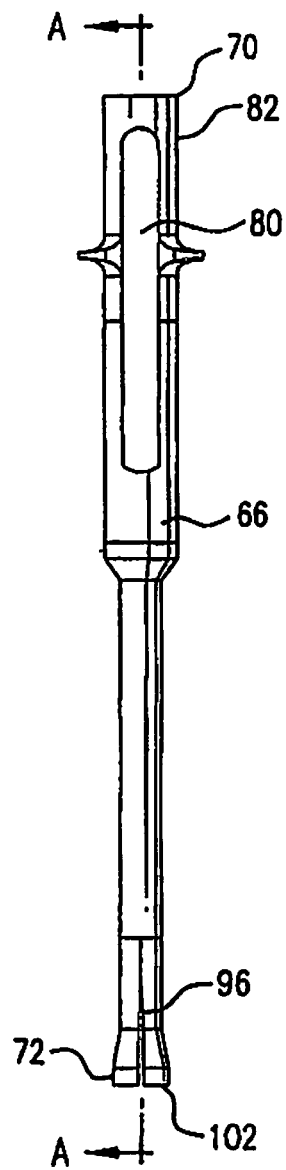
FIG. 7A shows a front view of a bone screw locking device component of the system with the locking device component configured to be moved into an operational connection with the screw component.
Figure 7B:
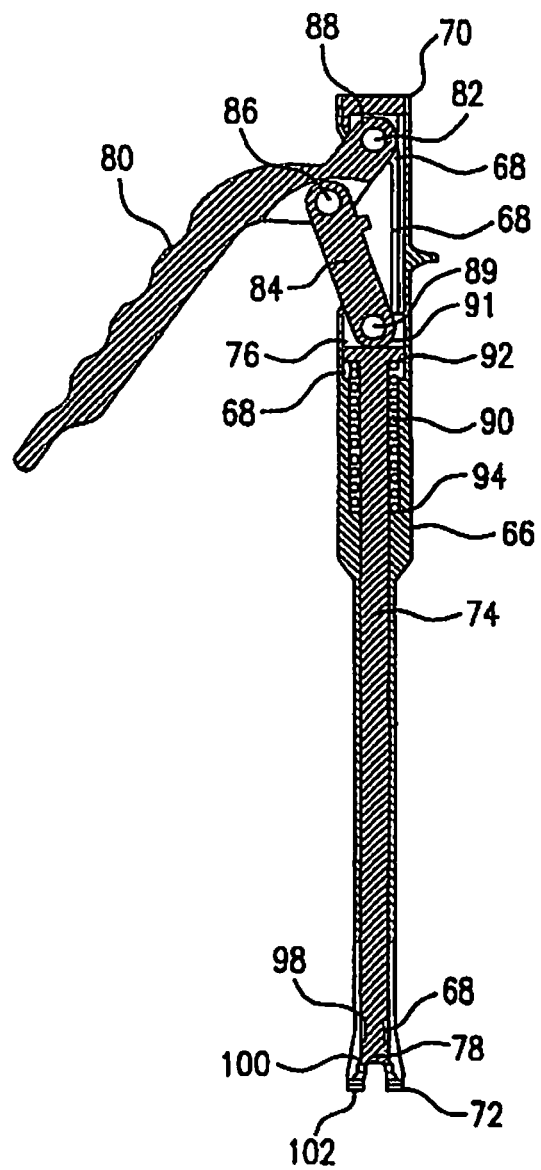
FIG. 7B is a cross-sectional view along section line A-A of FIG. 7A showing the locking device component of the system with the locking device component configured to be moved into an operational connection with the screw component.

To facilitate locking the novel screw 3 component of the system the locking device 7 component is provided with specific elements which are configured to connect to and interact with complementary elements of the screw 3. As best shown in FIGS. 2D, 5, 6, 7A-B and 8, the locking device 7 is an elongated surgical instrument having a locking device housing 66 that defines a locking device lumen 68, which extends from the locking device first end 70 to the full length of device 7 exiting from the locking device housing 66 at the locking device second end 72. As best shown in the cross-sectional views of FIGS. 7B and 8, there is contained within the locking device lumen 68 a locking device push rod 74. The locking device push rod 74 has a push rod first end 76 and a push rod second end 78 and is configured and dimensioned to slidably move within the longitudinal axis of the elongated lumen 68 of the locking device 7. The mechanism for actuating movement of the locking device push rod 74 within the lumen 68 is best seen in FIGS. 7B and 8. Movement of the push rod 74 is initiated by a push rod activator 80, which is preferably a lever action handle that is pivotally anchored adjacent the first end 70 of the locking device 7 at a handle pivot point 82. The actuator handle 80 is operationally connected to the push rod first end 76 via a locking device connecting arm 84. The connecting arm 84 is pivotally connected at a first pivot point 86 to a position adjacent and just distal to the proximal end 88 of the actuator handle 80. The connecting arm 84 is also pivotally connected at a second pivot point 89, which is located at the opposite or distal end 91 of the connecting arm 84. Thus the connecting arm 84 provides an operational link for the translation of rotational lever movement of the actuator handle 80 to downward piston-like movement of the locking device push rod within the locking device lumen 68. As the handle 80 is pivotally rotated inward toward the locking device housing 66, the pivotally attached connecting arm 84 is also moved inward, that inward movement producing a pushing force against the second pivot point 89 and thereby forcing the push rod 74 downward within the locking device lumen 68. An opposite outward rotational movement of the actuator handle 80 away from the locking device housing 66 pulls the connecting arm 84 upward and away from the locking device lumen 68 and the push rod 74 contained therein. The second pivot point 89 connection between the connecting rod 84 and the push rod 74 translates this outward pulling motion into a longitudinal upward movement of the push rod 74 within the locking device lumen 68.

As best shown in FIG. 7B, the locking device push rod 74 is in contact with a push rod biasing member 90, which is preferably a coil spring disposed around the push rod 74 between the inner wall of the lumen 68 and the elongated shaft of the push rod 74. An upper retainer 92 defined by an undercut on the first end 76 of the push rod 74 and a lower retainer 94 defined by an inwardly projecting annular ledge on the inner wall of the lumen 68 serve to define the limit of movement of the push rod biasing member 90 as the lever action of the actuator handle 80 forces the push rod 74 downward through the lumen 68 thereby compressing the biasing member 90. The biasing member 90 provides counter force to the lever actuator 80 and assists in releasing the locking device from the screw 3 after locking.

The second end of the housing 66 of the locking device 7 is best shown in FIG. 7B and FIG. 8. A compression slit 96 (sec FIG. 7A) through opposing walls of the lower portion of the housing 66 purposely weakens the integrity of the walls of the housing 66 that define the portion of the lumen 68 immediately adjacent to the slit 96 so as to allow the lumen 68 to widen or narrow as required by the passage of the push rod 74 into the lower portion of the locking device lumen 68. Slits 96 facilitate mounting the locking instrument onto screw 3 by permitting the walls of the lower portion of housing 66 to spread apart to receive the upper portion of the screw 3 within the distal end of the locking device 7. The outer surface of the lower portion of the push rod 74 is provided with push rod recesses defined at specific points to coincide with push rod cam surfaces 100 that are defined as inward projections from the inner surface of the lower portion of the locking device housing 66. In operation, as the push rod 74 is forced downward through the locking device lumen 68, the interaction of the push rod recesses 98 with the push rod cam surfaces 100 has the effect of relaxing the compressive forces between the push rod 74 and the push rod cam surfaces 100 such that the compression slit 96 is permitted to narrow according to the tensile nature of the material of the locking device housing 66, which is such that the housing 66, though capable of flexion, naturally seeks to retain its shape. The locking device terminus 102 at the second end 72 of the locking device 7 defines inwardly directed grasping projections along at least a portion of the inner wall of the lumen 68. These grasping projections 104 are configured to fit beneath the tool receiving element or flange 62 of the screw 3 component of the system 1 and preferably at least partially seat within the annular gripping groove 64.

FIG. 8 most clearly shows the operational relationship of the grasping projections 104 of the locking device 7 and the flange 62 of the screw 3. In operation, as the push rod 74 moves downward through the lumen 68 such that the cam surfaces 100 no longer exert a compressive force on the push rod 74, the grasping projections 104 are permitted to move inwardly toward the center of the lumen 68 and exert a holding force on the under side of the flange 62 of the screw 3. As the push rod 74 continues downward through the lumen, the second end 78 of the push rod makes forcible contact with a spinal rod 12 forcing it into inner and outer connecting rod slots 50, 52 of the screw 3. The second end 78 of the push rod 74 also makes forcible contact with the upper surface of the inner housing 28 so as to provide a downward force relative to the outer housing 26 of the screw 3. The opposing upward force on the flange 62 of the outer housing 26 of the screw 3 created by grasping projections 104 engaging annular flange 62 and the downward force of the push rod 74 on the inner housing 28 of the screw 3 results in a relative upward sliding motion of the outer housing 26 around the circumference of the inner housing 28. As this occurs, the resulting outer housing 26 compressive forces on the inner housing 28 of the screw 3, as described in detail earlier, serve to lock the screw head 18 of the screw 3 into a fixed position relative to the articulation recess 38 of the screw inner housing 28 and to lock the rod 12 relative to the inner housing 28. As discussed earlier, a partial lock position is contemplated in which limited motion of the articulating head of the screw and of rod 12 within the inner rod connecting rod slot 52 of the screw 3 is permitted. The partial lock position can be identified by the user by providing a visual cue or indicia on the actuator handle 80 or by providing tactile or audible feedback to the user as the actuator handle 80 moves the mechanism past a cam or other frictional contact within the mechanism. The visual, tactile or audible cue or indicia indicates to the user that the partial lock position has been achieved. Continued application of squeezing force on handle 80 provides further relative upward motion of the outer housing 26 over the surface of the inner housing 28 to exert additional compressive forces so as to lock the connecting rod 12 into a relative position to the screw. This fully locked position is best seen in FIGS. 2B, 3A, 4A and 8.

The Unlocking Device Component

Figure 9:
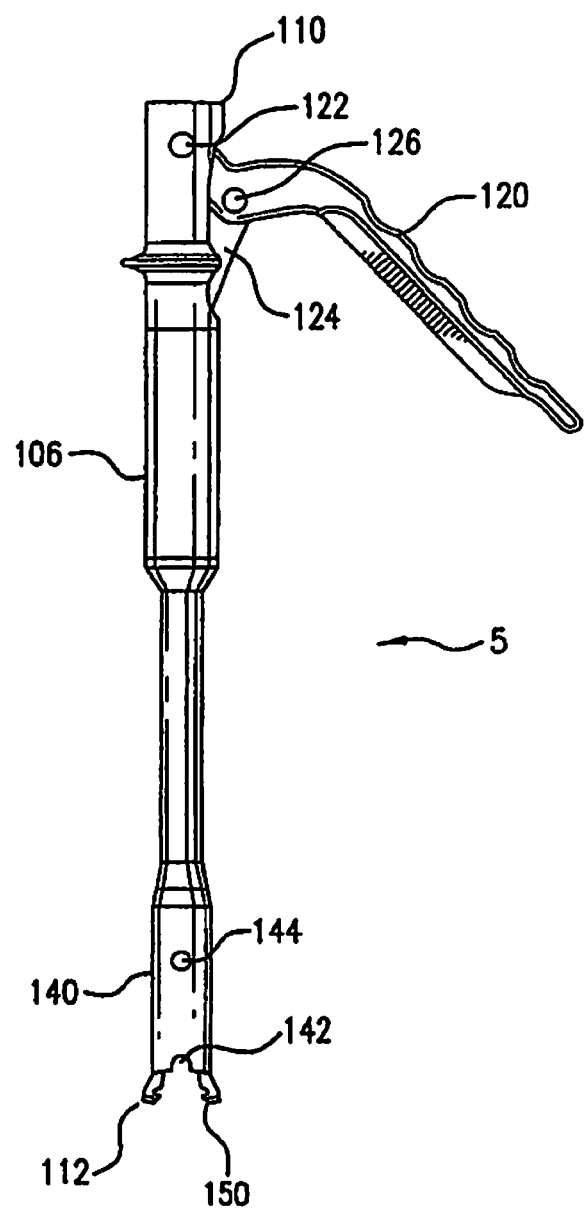
FIG. 9 shows a side view of a bone screw unlocking device component of the system.
Figure 10:
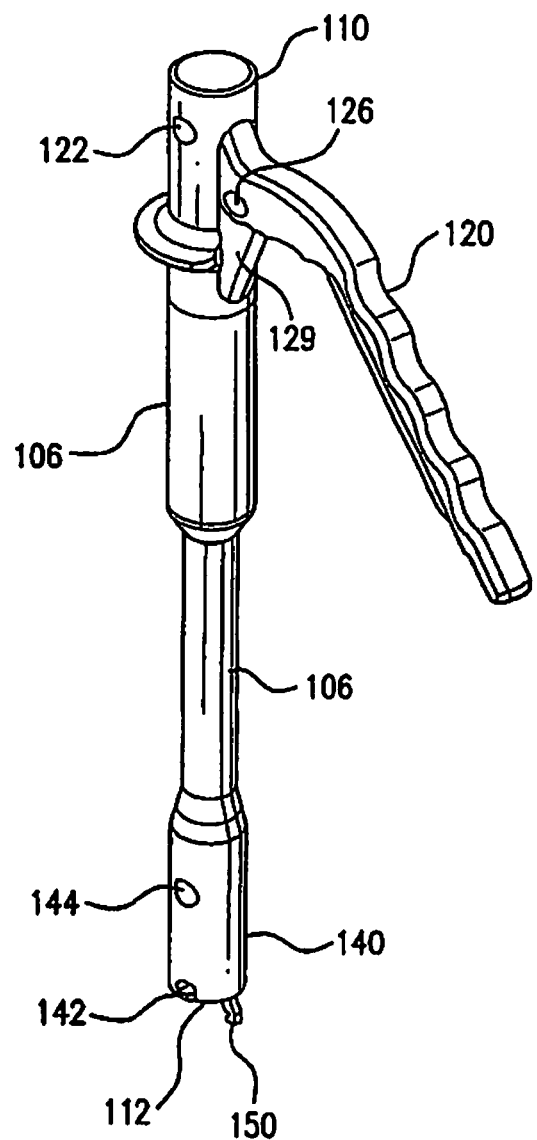
FIG. 10 shows an isometric view of a bone screw unlocking device component of the system.
Figure 11A:
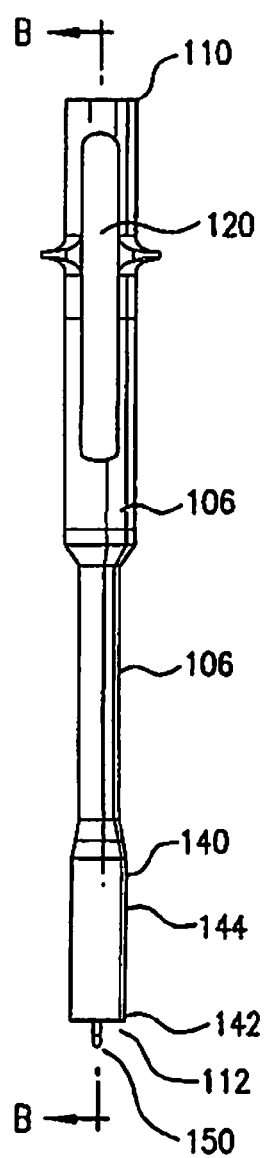
FIG. 11A shows a front view of a bone screw unlocking device component of the system with the unlocking device component positioned and ready to be moved into an operational connection with the screw component.
Figure 11B:
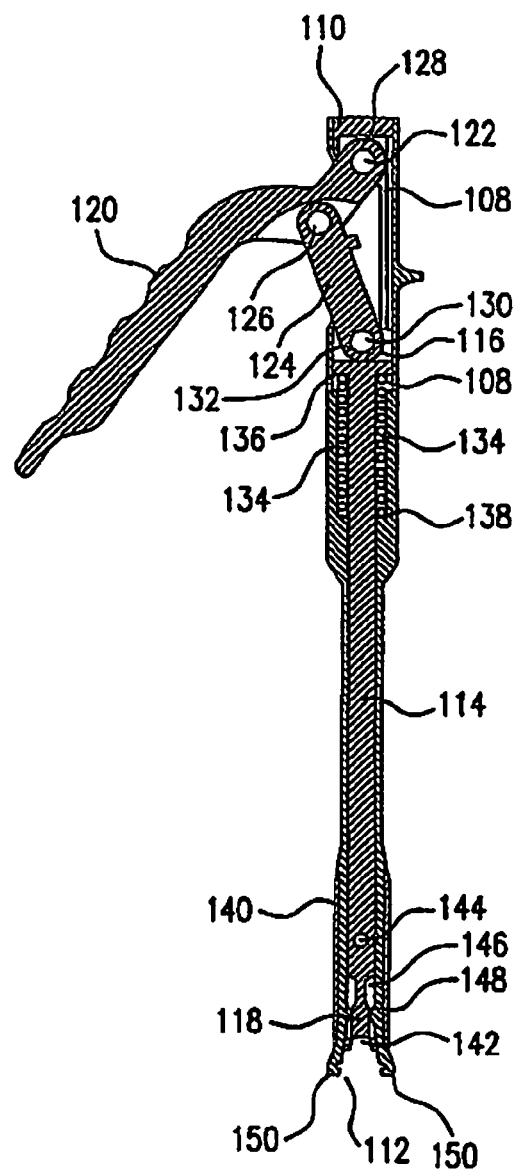
FIG. 11B is a cross-sectional view along section line B-B of FIG. 11A showing the unlocking device component of the system, with the unlocking device component positioned and ready to be moved into an operational connection with the screw component.

To facilitate unlocking the novel screw 3 component of the system 1, the unlocking device 5 component is provided with specific elements which are configured to connect to and interact with complementary elements of the screw 3. As best shown in FIGS. 2C and 9-12, the unlocking device 5 is an elongated surgical instrument having an unlocking device housing 106 that defines an unlocking device lumen 108 which extends from the unlocking device first end 110 to the full length of unlocking device 5 exiting from the unlocking device housing 106 at the locking device second end 112. As best shown in the cross-sectional views of FIGS. 11B and 12, there is contained within the unlocking device lumen 108 an unlocking device push rod 114. The unlocking device push rod 114 has an unlocking device push rod first end 116 and an unlocking device push rod second end 118 and is sized and configured to slidably move along the longitudinal axis of the unlocking device elongated lumen 108 of the unlocking device 5. The mechanism for actuating movement of the unlocking device push rod 114 within the lumen 108 is best seen in FIGS. 11B and 12. Movement of the unlocking device push rod 114 is initiated by an unlocking device push rod activator 120, which is preferably a lever action handle that is pivotally anchored to the first end 110 of the unlocking device 5 at a handle pivot point 122. The unlocking device actuator handle 120 is operationally connected to the push rod first end 116 via a locking device connecting arm 124. The connecting arm 124 is pivotally connected at a first pivot point 126 to a position adjacent and just distal to the proximal end 128 of the unlocking device actuator handle 120. The connecting arm 124 is also pivotally connected at a second pivot point 130, which is located at the opposite or distal end 132 of the connecting arm 124. This second pivot point 130 connection transfers lever movement of the unlocking device actuator handle 120 to the unlocking device push rod first end 116, where the pivotal connection 130 forces the unlocking device push rod 114 longitudinally downward within the unlocking device lumen 108 toward the second end 112 of the unlocking device 5. An opposite movement of the actuator handle 120 of the unlocking device 5 serves to pull the connecting arm 124 upward and results in an upward movement of the unlocking device push rod 114 within the lumen 108.

As best shown in FIG. 11B, the unlocking device push rod 114 is in contact with an unlocking device push rod biasing member 134, which is preferably a coil spring disposed around the push rod 114 between the inner wall of the lumen 108 and the elongated shaft of the unlocking device push rod 114. An upper retainer 136 defined by an undercut on the first end 116 of the unlocking device push rod 114 and a lower retainer 138 defined by an inwardly projecting annular ledge on the inner wall of the unlocking device lumen 108 serve to define the limit of movement of the unlocking device push rod biasing member 134 as the lever action of the unlocking device actuator handle 120 forces the push rod 114 downward through the lumen 108 thereby compressing the unlocking device push rod biasing member 134.

As best shown in FIG. 11B and FIG. 12, an outer sleeve 140 is provided in a slidable circumferential disposition around at least a portion of the lower part of the unlocking device 5, adjacent to the second end 112. As best shown in FIGS. 9, 10 and 11B, this outer sleeve 140 is, at its bottom edge, provided with a connecting rod slot 142, which is sized and configured to permit easy through passage of a spinal connecting rod 12. The unlocking device outer sleeve 140 is connected to the unlocking device push rod 114 by an outer sleeve connecting pin, which provides a coordinated movement connection of the push rod 114 and the outer sleeve 140 through a connecting pin slot 142 defined through the wall of the lower portion of the unlocking device housing 106. Thus, in operation, a compressive movement of the unlocking device actuator handle 120 through the pivotal connection to the connecting arm 124 causes a downward movement of the unlocking device push rod 114 through the lumen 108 and that same downward movement is communicated to the outer sleeve 140 by the mechanical connection of the push rod 114 via the connecting pin 144. Similarly, an outward movement of the actuator handle 120 will result in a coordinated longitudinal upward movement of the unlocking device push rod 114 and its connected outer sleeve 140.

As best shown in FIGS. 11B and 12, the outer surface of the lower portion of the unlocking device push rod 114 is provided with unlocking device push rod recesses 146 defined at specific points to coincide with unlocking device push rod cam surfaces 148 that are defined as inward projections from the inner surface of the lower portion of the unlocking device housing 106.

The second end of the unlocking device housing 106 terminates in at least a pair of opposing screw grasping elements 150 that are sized and configured to easily pass through the inner housing access slots 60 that are defined in the outer housing 26 of the screw 3. Passage of the grasping elements 150 through the inner housing access slots 60 permits the grasping elements 150 to make an operational connection with the inner housing tool receptor 61. As best shown in FIGS. 11B and 12, the configuration of the grasping elements 150 and the complimentary inner housing tool receptor 61 facilitates the holding and the upward pulling of the inner housing 28 of the screw while the outer sleeve 140 of the unlocking device 5 is pressed against the top of the outer housing 26 when the operator actuates the handle 120 of the unlocking device so as to unlock the screw 3. This relative motion of the outer housing 26 and the inner housing 28 of the screw 3, as described earlier has the effect of either partially unlocking the screw or fully unlocking the screw 3 as desired depending upon whether the handle 120 is partially or fully squeezed.

In operation, when the operator of the unlocking device 5 selectively moves the unlocking device actuator handle 120 so as to push the unlocking device push rod 114 downward through the unlocking device lumen 108, the surfaces defining the unlocking device push rod recesses 146 interact with the unlocking device push rod cam surfaces 148 defined by the unlocking device housing 106 to move the grasping elements 150 into a holding connection with the inner housing tool receptor 61. This motion of the unlocking device push rod 114 at the same time serves to move the connected outer sleeve 140 downward against the outer housing 26 of the screw 3. This pushing downward on the outer housing 26 of the screw 3 while pulling upward on the inner housing 28 of the screw 3, serves to partially or fully unlock the screw 3.

FIG. 12 most clearly shows the operational relationship of the grasping elements 150 of the unlocking device 5 and the inner housing tool receptor 61 of screw 3. As discussed earlier in detail, a partial lock or partial unlock position can be permitted which allows limited motion of the rod 12 within the inner rod connecting rod slot 52 of the screw 3. As with the locking device 7 of the system 1, the unlocking device 5 can be provided with a way of identifying when the unlocking device 5 is in a partial unlocked position by providing a visual cue on the unlocking device actuator handle 120 or by providing tactile feedback to the user as the actuator handle 120 moves the mechanism past a cam or other frictional contact within the mechanism. Further relative upward motion of the inner housing 28 within the outer housing 26 relieves additional compressive forces so as to unlock the connecting rod 12 into a relative position to the screw. This fully unlocked position is best seen in FIGS. 1, 2A, 3B, 4B and 12.

The materials used to construct the present invention are those which have sufficient strength, resiliency, and biocompatibility as is well known in the art for such devices. Methods of manufacture of such surgical implant devices are also well known in the art. By way of example only, suitable materials for screw 3 include titanium, titanium alloys including Nitinol, stainless steel, and cobalt chrome alloys. The locking and unlocking instruments are intended to be cleaned, re-sterilized and used in multiple procedures, and so may be made of stainless steel or other suitable materials for this purpose. Because the locking and unlocking instruments are not intended to be implanted in the body, implant grade materials are not required and the additional expense for such materials may not be justified; however, such materials may be used if desired.

In use, a surgeon accesses the patient's spine in a known manner either using open surgical techniques or minimally invasive techniques, and prepares the bone to receive screws, as is deemed appropriate under the circumstances. Multiple taper lock screws are inserted into bone according to the operative plan of the surgeon, and a rod is placed in or adjacent the inner housing recess and extends through slots 50, 52 to adjacent screws. The surgeon then uses the locking instrument to lock or partially lock each screw to the rod. Advantageously, the surgeon may partially lock each screw and before finishing the locking step may readjust the arrangement of the screws and rods to better suit the surgical situation. It has been found that partially locking the screws and then readjusting the positioning of the rod and screws may permit the surgeon to obtain superior surgical results. That is, with prior screws and rods, if the surgeon attempted to partially lock the screws, i.e., partially tighten the screw or nut, and then to readjust the construct, the construct under the forces exerted by the anatomy would not remain in position to allow the surgeon to return and tighten the screws to lock the screws. With the taper lock screws and the locker disclosed herein, the surgeon may partially lock the screws so that as he or she subsequently adjusts the screws and rods the construct will stay in the adjusted position. The partial locked position of the screw provides great flexibility to the surgeon in making any adjustments deemed necessary such as, but not limited to, compression, distraction, and rotation of the entire construct or of individual bodies associated with the screws. After completing whatever adjustments are required, the surgeon can then fully lock each screw with the locking instrument. This technique is particularly advantageous for deformity cases, where long constructs need to be adjusted during surgery in order to obtain the best clinical results. As mentioned after final positioning, with the plurality of screws in the partial lock position, the surgeon uses the locking instrument to fully lock each screw and rod together in any order chosen by the surgeon. The convenient engagement features on the screw and locking tool enable the surgeon to quickly mount the locking instrument to each screw and fully lock each screw in rapid sequence. In contrast, conventional systems require the surgeon to apply a predetermined amount of torque to each screw, which is time consuming and more tedious than the present quick lock system. Should the surgeon fully lock the screw and thereafter need to adjust the screw, the unlocking instrument may be used to partially or fully unlock the screw to permit adjustment. In the event of revision surgery, the unlocking instrument may be used to partially or fully unlock the screw, and the surgeon may then adjust or revise the construct as necessary. It should be noted that in the event of revision surgery, the provision of the proximal flange on the outer housing to engage the locking instrument can be particularly advantageous. Not only does the proximal flange facilitate better visibility and access during initial implantation by engaging the locking and unlocking instruments in a proximal location away from the bone bed, during revision surgery the proximal location of the features of the inner and outer housing for engaging the locking and unlocking instruments facilitates accessing those features more readily during revision surgery. That is the surgeon need not remove tissue around the screw all the way to bone at the bottom of the screw in order to attempt to mount the locking and more particularly the unlocking instrument over the screw.

It is contemplated to provide the system 1, including the multi-planar taper lock screw 3, the locking device 7 and the unlocking device 5 as part of a kit for use in a surgical process, the kit comprising at least two of the screws 3 and at least some of the associated tools for using the screws to connect a surgical rod to adjacent bones or bone fragments. In addition, the kit can contain surgical rods, such as, for example, spinal rods. Additional devices such as cross-connectors, hooks or links can also be included in the kit.

Each of the embodiments described above are provided for illustrative purposes only and it is within the concept of the present invention to include modifications and varying configurations without departing from the scope of the invention that is limited only by the claims included herewith.

What is claimed is:

1. A taper lock screw comprising:
a screw including a shaft and a superiorly positioned screw head;
an inner housing supporting the screw head of the screw and including an inner surface, an outer surface, and an uppermost portion;
an outer housing including an inner surface, an outer surface, and an uppermost portion, the inner surface of the outer housing circumferentially disposed around, and in contact with, at least a portion of the outer surface of the inner housing, the outer housing slidably movable relative to the inner housing to selectively secure a connecting rod within the inner housing and transition the taper lock screw between an unlocked position and a locked position, the inner surface of the outer housing and the outer surface of the inner housing defining a gap therebetween, wherein the gap has a first dimension in the unlocked position and a larger dimension in the locked position, and wherein there is relative flexing movement between the outer housing and the inner housing in response to the transition of the taper lock screw between the unlocked and locked positions; and
an annular flange projecting outwardly from the uppermost portion of the outer housing, the annular flange having an uppermost portion, uppermost portions of the connecting rod and the flange being substantially coplanar when the taper lock screw is in the locked position.

2. The taper lock screw of claim 1, wherein the flange is positioned to overhang a circumferentially defined annular gripping groove that is configured to facilitate grasping contact of a grasping tool for facilitating locking of the taper lock screw.

3. The taper lock screw of claim 1, wherein the flange is positioned to overhang an annular gripping groove circumferentially defined in the outer surface of at least a portion of the outer housing.

4. The taper lock screw of claim 1, wherein an articulation recess is defined in a lower portion of the inner housing, and wherein the articulation recess retains the screw head of the screw within the inner housing while enabling the screw head to rotate within the articulation recess.

5. The taper lock screw of claim 4, wherein the articulation recess includes at least one contact surface positioned against the screw head.

6. The taper lock screw of claim 4, wherein the inner housing defines a rod slot in the uppermost portion of the inner housing, the rod slot adapted to receive the connecting rod, the rod slot and the articulation recess being coaxially aligned relative to a longitudinal axis defined through the inner housing that extends through the uppermost portion of the inner housing and the lower portion of the inner housing.

7. The taper lock screw of claim 1, wherein the outer housing is slidable relative to the inner housing to contact the inner housing with sufficient compressive force to enable the inner housing to contact and secure the connecting rod within the inner housing.

8. The taper lock screw of claim 1, wherein the outer housing is positionable relative to the inner housing to compress the outer housing against the inner housing to transition the taper lock screw to a partially locked position for sufficiently locking the taper lock screw while enabling movement of the connecting rod within the inner housing.

9. The taper lock screw of claim 1, wherein the uppermost portion of the flange and the uppermost portion of the connecting rod are substantially coplanar with the uppermost portion of the inner housing in the locked position of the taper lock screw.

10. The taper lock screw of claim 1, wherein the uppermost portion of the flange and the uppermost portion of the connecting rod are substantially coplanar with the uppermost portion of the outer housing in the locked position of the taper lock screw.

11. The taper lock screw of claim 1, wherein the uppermost portion of the connecting rod is substantially coplanar with the uppermost portion of the inner housing in the locked and unlocked positions of the taper lock screw.

12. The taper lock screw of claim 1, wherein at least one of the outer housing and the inner housing is configured to flex in response to the transition of the taper lock screw between the unlocked and locked positions.

13. The taper lock screw of claim 1, wherein the gap is an enclosed space between the inner and outer housings.

14. A taper lock screw comprising:
a screw including a shaft and a superiorly positioned screw head;
an inner housing supporting the screw head of the screw and including an inner surface, an outer surface, and an uppermost portion;
an outer housing including an inner surface, an outer surface, and an uppermost portion, the inner surface of the outer housing circumferentially disposed around, and in contact with, at least a portion of the outer surface of the inner housing, the outer housing slidably movable relative to the inner housing to selectively secure a connecting rod within the inner housing and transition the taper lock screw between an unlocked position and a locked position, the inner surface of the outer housing and the outer surface of the inner housing defining a gap therebetween; and
an annular flange projecting outwardly from the uppermost portion of the outer housing, the annular flange having an uppermost portion, uppermost portions of the connecting rod and the flange being substantially coplanar when the taper lock screw is in the locked position, the annular flange having a diameter greater than a largest diameter of the outer housing.

15. The taper lock screw of claim 14, wherein an articulation recess is defined in a lower portion of the inner housing, the articulation recess retaining the screw head of the screw within the inner housing while enabling the screw head to rotate within the articulation recess.

16. The taper lock screw of claim 15, wherein the inner housing defines a rod slot in the uppermost portion of the inner housing, the rod slot adapted to receive the connecting rod, the rod slot and the articulation recess being coaxially aligned relative to a longitudinal axis defined through the inner housing that extends through the uppermost portion of the inner housing and a lower portion of the inner housing.

17. The taper lock screw of claim 14, wherein the uppermost portion of the flange and the uppermost portion of the connecting rod are substantially coplanar with the uppermost portion of the inner housing in the locked position of the taper lock screw.

18. The taper lock screw of claim 14, wherein the outer housing is positionable relative to the inner housing to compress the outer housing against the inner housing to transition the taper lock screw to a partially locked position for sufficiently locking the taper lock screw while enabling movement of a connecting rod within the inner housing.

19. The taper lock screw of claim 14, wherein the annular flange projects outwardly from an uppermost portion of the outer surface of the outer housing.

20. The taper lock screw of claim 14, wherein the gap is an enclosed space between the inner and outer housings.

* * * * *